(12) United States Patent
Sharma et al.

(10) Patent No.: US 11,430,547 B2
(45) Date of Patent: Aug. 30, 2022

(54) SYSTEMS AND METHODS FOR VIRTUAL CLINICAL TRIALS

(71) Applicant: Sharecare AI, Inc., Palo Alto, CA (US)

(72) Inventors: Srivatsa Akshay Sharma, Santa Clara, CA (US); Walter Adolf De Brouwer, Los Altos, CA (US); Gabriel Gabra Zaccak, Cambridge, MA (US); Chethan R. Sarabu, Morgan Hill, CA (US); Devin Daniel Reich, Olympia, WA (US); Marina Titova, Menlo Park, CA (US); Andrés Rodríguez Esmeral, Vancouver (CA)

(73) Assignee: Sharecare AI, Inc., Palo Alto, CA (US)

( * ) Notice: Subject to any disclaimer, the term of this patent is extended or adjusted under 35 U.S.C. 154(b) by 0 days.

(21) Appl. No.: 17/400,079

(22) Filed: Aug. 11, 2021

(65) Prior Publication Data
US 2022/0051762 A1    Feb. 17, 2022

Related U.S. Application Data

(60) Provisional application No. 63/064,624, filed on Aug. 12, 2020.

(51) Int. Cl.
*G16H 10/20* (2018.01)
*H04L 9/08* (2006.01)
(Continued)

(52) U.S. Cl.
CPC ............ *G16H 10/20* (2018.01); *G06F 7/483* (2013.01); *G06F 7/523* (2013.01); *G06F 7/588* (2013.01); *H04L 9/0861* (2013.01)

(58) Field of Classification Search
CPC ........ G16H 10/00–65; G06F 7/00–785; H04L 9/00–38
See application file for complete search history.

(56) References Cited

U.S. PATENT DOCUMENTS

| 2014/0257047 | A1* | 9/2014 | Sillay | A61B 5/4082 600/301 |
| 2016/0357173 | A1* | 12/2016 | Foschini | G16H 10/20 |
| 2020/0110897 | A1 | 4/2020 | Wainblat et al. | |

FOREIGN PATENT DOCUMENTS

WO    2019142238 A1    7/2019

OTHER PUBLICATIONS

Bourse et al., "Improved Secure Integer Comparison via Homomorphic Encryption," (2017) in 27 pages.
(Continued)

*Primary Examiner* — Mohammad A. Nilforoush
(74) *Attorney, Agent, or Firm* — Haynes Beffel & Wolfeld LLP; Ernest J. Beffel, Jr.; Sikander M. Khan

(57) ABSTRACT

The technology disclosed relates to a system and method for assigning participants to groups in a clinical trial. The system includes a federated server configured with group assignability data specifying a plurality of groups assignable to participants in a clinical trial and group distribution data specifying distribution of the participants into groups. The groups include at least one placebo group and one or more treatment groups. The system includes an intervention server configured to generate group encryption keys for encrypting the group assignability data. The system includes edge devices of each of the participants. The edge devices are in communication with the federated server.

20 Claims, 10 Drawing Sheets

(51) Int. Cl.
  *G06F 7/523* (2006.01)
  *G06F 7/58* (2006.01)
  *G06F 7/483* (2006.01)

(56) References Cited

OTHER PUBLICATIONS

De Cock et al., "Fast, Privacy Preserving Linear Regression over Distributed Datasets based on Pre-Distributed Data", (2015) © 2015 ACM. ISBN 978-1-4503-3826-04/15/10 . . . 15.00 DOI: http://dx.doi.org/10.1145/2808769.2808774, retrieved from http://faculty.washington.edu/mdecock/papers/mdecock2015a.pdf, in 12 pages.
De Cock et al., "Efficient and Private Scoring of Decision Trees, Support Vector Machines and Logistic Regression Models based on Pre-Computation", (2017) retrieved from https://eprint.iacr.org/2016/736.pdf, in 14 pages.
De Cock et al., "High Performance Logistic Regression for Privacy-Preserving Genome Analysis", (2020) arXiv:2002.05377v2 [cs.CR], retrieved from https://arxiv.org/pdf/2002.05377.pdf, in 14 pages.
Goyal, Introduction to Cryptography, Lecture 23—Secure Computation II, dated Apr. 27, 2018, 6 pages.
PCT/US2021/045725—International Search Report and Written Opinion, dated Nov. 26, 2021, 17 pages.

\* cited by examiner

Selection Phase - Compute Secrets

Selection Phase - Combine Secrets

SYSTEMS AND METHODS FOR VIRTUAL CLINICAL TRIALS

PRIORITY APPLICATION

This application claims the benefit of U.S. Patent Application No. 63/064,624, titled "Systems and Methods for Virtual Clinical Trials," filed Aug. 12, 2020. The provisional application is hereby incorporated by reference for all purposes.

INCORPORATIONS

The following materials are incorporated by reference as if fully set forth herein:

U.S. Provisional Patent Application No. 62/734,840, titled, "HASH-BASED EFFICIENT COMPARISON OF SEQUENCING RESULTS," filed Sep. 21, 2018;

U.S. Provisional Patent Application No. 62/734,872, titled, "BIN-SPECIFIC AND HASH-BASED EFFICIENT COMPARISON OF SEQUENCING RESULTS," filed Sep. 21, 2018;

U.S. Provisional Patent Application No. 62/734,895, titled, "ORDINAL POSITION-SPECIFIC AND HASH-BASED EFFICIENT COMPARISON OF SEQUENCING RESULTS," filed Sep. 21, 2018;

U.S. Nonprovisional patent application Ser. No. 16/816,153 titled, "SYSTEM AND METHOD WITH FEDERATED LEARNING MODEL FOR MEDICAL RESEARCH APPLICATIONS," filed Mar. 11, 2020;

U.S. Provisional Patent Application No. 62/942,644 titled, "SYSTEMS AND METHODS OF TRAINING PROCESSING ENGINES," filed Dec. 2, 2019;

U.S. patent application Ser. No. 17/109,118, titled, "SYSTEMS AND METHODS OF TRAINING PROCESSING ENGINES," filed Dec. 1, 2020;

U.S. Provisional Patent Application No. 62/883,070 titled, "ACCELERATED PROCESSING OF GENOMIC DATA AND STREAMLINED VISUALIZATION OF GENOMIC INSIGHTS," filed Aug. 5, 2019;

U.S. patent application Ser. No. 16/985,183, titled, "ACCELERATED PROCESSING OF GENOMIC DATA AND STREAMLINED VISUALIZATION OF GENOMIC INSIGHTS," filed Aug. 4, 2020;

U.S. Provisional Patent Application No. 62/975,177, titled, "ARTIFICIAL INTELLIGENCE-BASED DRUG ADHERENCE MANAGEMENT AND PHARMACOVIGILANCE," filed Feb. 11, 2020;

U.S. patent application Ser. No. 17/174,323, titled, "ARTIFICIAL INTELLIGENCE-BASED DRUG ADHERENCE MANAGEMENT AND PHARMACOVIGILANCE," filed Feb. 11, 2021;

U.S. Provisional Patent Application No. 62/810,549, titled, "SYSTEM AND METHOD FOR REMOTE MEDICAL INFORMATION EXCHANGE," filed Feb. 26, 2019;

U.S. patent application Ser. No. 16/802,485, titled, "SYSTEM AND METHOD FOR REMOTE MEDICAL INFORMATION EXCHANGE," filed Feb. 26, 2020;

U.S. Nonprovisional patent application Ser. No. 15/946,629, titled "IMAGE-BASED SYSTEM AND METHOD FOR PREDICTING PHYSIOLOGICAL PARAMETERS," filed on Apr. 5, 2018;

U.S. Provisional Application No. 62/481,691, titled "METHOD OF BODY MASS INDEX PREDICTION BASED ON SELFIE IMAGES," filed on Apr. 5, 2017;

U.S. Provisional Patent Application No. 62/883,639, titled "FEDERATED CLOUD LEARNING SYSTEM AND METHOD," filed on Aug. 6, 2019;

U.S. Provisional Patent Application No. 62/816,880, titled "SYSTEM AND METHOD WITH FEDERATED LEARNING MODEL FOR MEDICAL RESEARCH APPLICATIONS," filed on Mar. 11, 2019;

U.S. Provisional Patent Application No. 62/671,823, titled "SYSTEM AND METHOD FOR MEDICAL INFORMATION EXCHANGE ENABLED BY CRYPTO ASSET," filed on May 15, 2018;

U.S. Nonprovisional patent application Ser. No. 16/167,338, titled "SYSTEM AND METHOD FOR DISTRIBUTED RETRIEVAL OF PROFILE DATA AND RULE-BASED DISTRIBUTION ON A NETWORK TO MODELING NODES," filed on Oct. 22, 2018; and U.S. Nonprovisional patent application Ser. No. 17/319,025, titled "Privacy Interface for Data Loss Prevention via Artificial Intelligence Models," filed on May 12, 2021.

FIELD OF THE TECHNOLOGY DISCLOSED

The technology disclosed relates to use of privacy techniques to setup and conduct blinded virtual clinical trials.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Clinical research is medical research involving people. There are two types of clinical research, observational studies, and clinical trials. Observational studies observe people in normal settings. Researchers gather information, group volunteers according to broad characteristics, and compare changes over time. These studies may help identify new possibilities for clinical trials. Clinical trials are research studies performed in people that are aimed at evaluating a medical, surgical, or behavioral intervention. They are the primary way that researchers find out if a new treatment, like a new drug or diet or medical device (for example, a pacemaker or a face mask for sleep apnea) is safe and effective in people. Clinical trials advance through phases to test a treatment. Several parties are involved in clinical trials such as a principal investigator (PI) and her team, participants, a pharmacy, or a distributor that can distribute drugs or medical devices to participants on behalf of the principal investigator and her team.

Clinical trials are expensive to conduct and require considerable planning and effort. The participants may be divided into two or more groups. The distribution of participants in groups is random and often double blinded, i.e., the researchers (PI and her team) do not know which participant is assigned to which group and the participants do know which group they are assigned to. One or more groups may be given the experimental drugs or medical devices that are being investigated. This group of participants is referred to as an intervention group or a real group. At least one group of participants is provided a fake treatment which is also referred to as a placebo. A placebo is defined as any therapy used for its nonspecific, psychological, or psychophysiological effect and is without specific activity of the condition being treated (Shapiro & Morrison, 1978, "The Placebo Effect in Psychotherapy and Behavior Change"). The participants are randomly assigned to intervention and placebo groups. In double blind clinical trials neither the PI and her team nor the participant knows whether a specific participant belongs to the intervention or the placebo group. Typically, a trusted third-party knows about this assignment and is responsible for providing the correct therapy to a participant according to the participant's assignment to intervention or placebo group. Biases have been observed in real world clinical trials in which participants favor assignment to an intervention group instead of a placebo group. As participants do not like to visit hospitals or clinics to avoid getting infected by viruses such as COVID-19, the researchers are motivated to conduct clinical trials in a virtual or decentralized environment.

Virtual or decentralized clinical trials can be conducted without any physical interaction between the parties. In addition, the virtual clinical trials are convenient for participants and researchers to set up and conduct the trial. Participants can easily enroll in a clinical trial using a software application. However, to conduct the clinical trial at various levels of privacy (such as a single blinded, double blinded, etc.), it is required that the entire setup and data collection steps of the trial be conducted in a blinded manner. To meet the privacy (or blinding) requirements, the researchers and participants should not know which group (intervention or placebo), a participant is assigned to. In addition to that, clinical trials have specific assignment requirements specifying a ratio of participants to be assigned to different groups. As the assignment of participants to groups is anonymous and not disclosed to researchers and participants, it is a challenge to ensure correct assignment of participants to groups while maintaining the privacy level required by the clinical trial.

An opportunity arises to develop a system that can not only randomly assign participants to different groups of a clinical trial but also achieve the assignment ratio requirement and other parameters for intervention and placebo groups set by the researcher.

DETAILED DESCRIPTION

Figure 1:
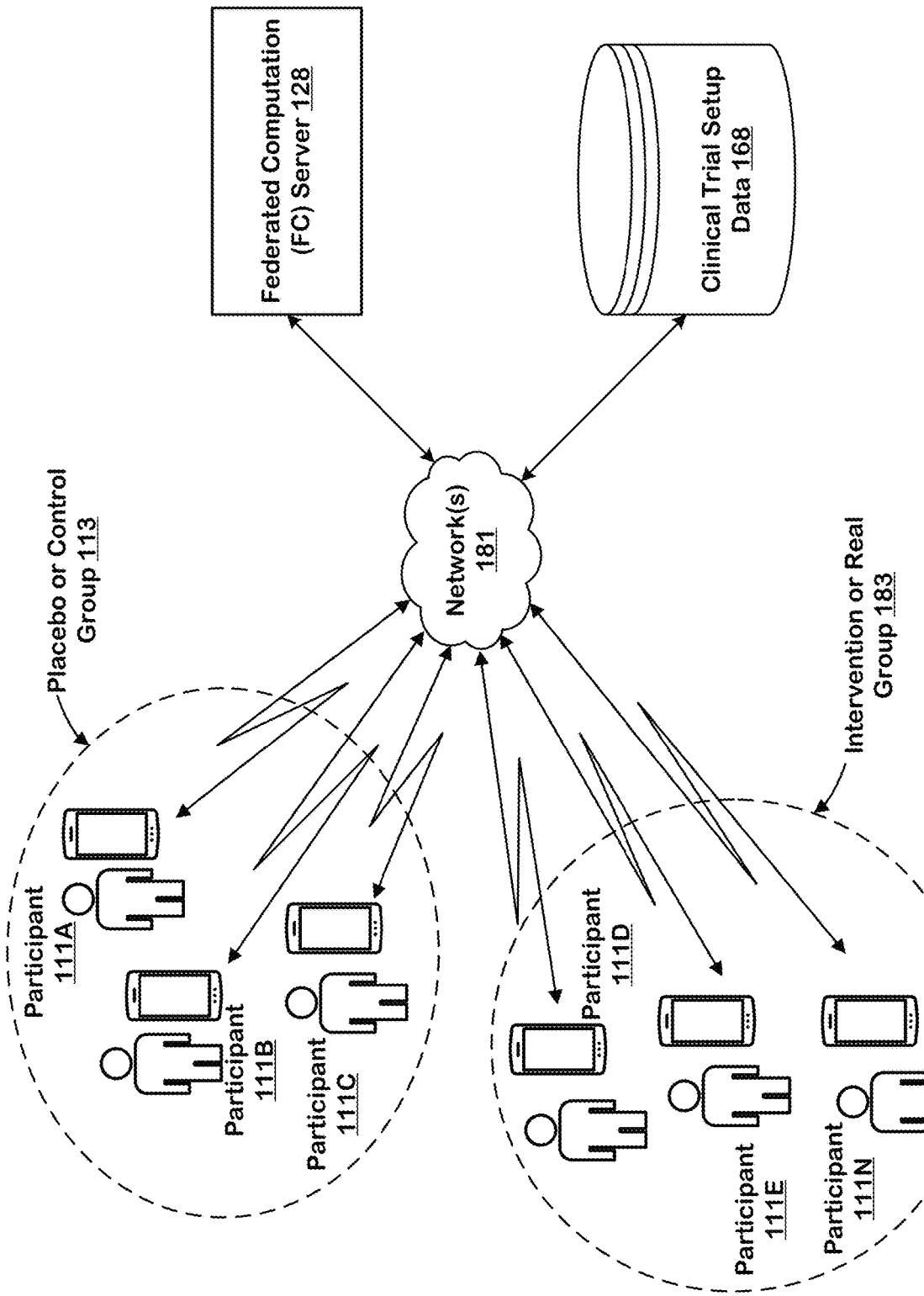
FIG. 1 illustrates an example environment in which the technology disclosed is used to conduct a virtual clinical trial.

The following discussion is presented to enable any person skilled in the art to make and use the technology disclosed and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown but is to be accorded the widest scope consistent with the principles and features disclosed herein.

INTRODUCTION

A blinded (or masked) clinical trial is a field of study of a drug (or any other treatment) in which the recipient does not know if he is receiving the real drug or a placebo (fake drug or treatment). Blinding is a procedure in clinical research in which one or more parties in a trial are kept unaware of which treatment arms (or groups) participants have been assigned to, i.e., which patient or participant in the study received which treatment. Blinding is an important aspect of any clinical trial done in order to avoid and prevent conscious and unconscious bias in the design and execution of the trial. The different parties involved in a clinical trial are all possible sources of bias. Examples of parties include participants or patients being treated, clinical staff or pharmacy administering the treatment, physician (or principal investigator, or researcher), and an analyst interpreting the clinical trial data. Note that the principal investigator may have a team of researchers, likewise a team of analysts can work on interpreting the trial data.

When conducting virtual or decentralized clinical trials, the parties in the clinical trial may not have any physical interaction with each other. However, the blinding requirements and random assignment of participants to treatment arms or groups need to be strictly followed for acceptance of results of clinical trials in the medical community. This is essential to gain the trust of physicians to adopt the new drug or the treatment therapy being investigated. Thus, a virtual clinical trial or decentralized clinical trial needs to provide a robust blinding mechanism to mask the parties from each other. In addition, the virtual clinical trial needs to provide reliable mechanisms to unblind the blinded data to give access to authorized analysts to interpret the clinical trial data. The blinding, unblinding, and randomness mechanisms in a virtual clinical trial need to follow strict privacy protocols in a planned manner to build the trust of the research community.

The technology disclosed provides a system that can implement a multi-phase virtual clinical trial process. In an initialization phase, various parties exchange information which can be used to compute the assignment of participants to treatment groups in a blinded manner. For example, in a double blinded clinical trial, to meet the blinding requirements, the system assigns participants to treatment groups such that the participants do not know about the assignment.

The server to which the edge devices of participants connect to also does not know the assignment of participants to groups in a double blinded clinical trial. The system includes a third-party server or an intervention server that is equivalent to clinical staff or pharmacy administering the treatment in a regular clinical trial. This server includes the logic to unblind the assignment data of participants to groups (or treatment arms) so that it can send correct treatment (real drug or placebo) to the participants.

In a setup and selection phases, the system can apply a variety of encryption techniques as building blocks to implementing different levels of privacy such as single, double, or triple blinding when selecting participants for treatment or intervention groups. The system allows the principal investigator or the researcher to identify a ratio of participants to be randomly assigned to various intervention groups or arms. The system includes logic to ensure that this ratio of assignment to intervention groups is met while maintaining the blinding between the parties. After the setup and selection phases, the edge devices collect trial data from participants using an app executing on the edge devices. The edge devices can also be connected to other wearable devices in the data collection process. When the trial is complete, the system includes logic to send the trial data in a secure and encrypted manner to an encrypted database which can only be accessed by authorized analysts to decrypt the data for analysis.

Environment

We describe a system for conducting virtual clinical trials with various levels of blinding. The system is described with reference to FIG. 1 showing an architectural level schematic of a system in accordance with an implementation. Because FIG. 1 is an architectural diagram, certain details are intentionally omitted to improve the clarity of the description. The discussion of FIG. 1 is organized as follows. First, the elements of the figure are described, followed by their interconnection. Then, the use of the elements in the system is described in greater detail.

FIG. 1 includes the system 100. This paragraph names labeled parts of system 100. The figure includes a federated computation (FC) server 128, a clinical trial setup database 168, participants 111A-111N. The participants can be divided into two or more groups. For example, in FIG. 1, the participants are divided into two groups: an intervention (or real) group 183 and a placebo (or control) group 113.

A network(s) 181 couples federated computation (FC) server 128, a clinical trial setup database 168, and participants 111A-111N. The participants can be divided into two or more groups. The participants have edge devices running an application (or app) that can be used to communicate to the FC server. The app can collect trial data and store it locally on the edge devices of respective participants. The clinical trial setup database 168 can contain setup data or configurations for the clinical trials. The setup data can specify values of various parameters for the clinical trial, such as participant selection criteria, assignment ratio of participants to different treatment groups, etc. The principal investigator can set values for different parameters of clinical trial. For example, the ratio of participants to be assigned to each group in the clinical trial. The setup data can also indicate the level of privacy (e.g., single blinded, double blinded, triple blinded, etc.) for the clinical trial.

Two key parameters for a clinical trial are randomization and blinding parameters. Randomization is the process by which a participant gets assigned to a control group (or control arm, or placebo arm) or an intervention group (or intervention arm, or real arm). Typically phase 2, 3, and 4 clinical trials have at least two groups, a control group and an intervention group. Principal investigator can decide the required number of groups for a clinical trial and the percentage of participants to be randomly selected per group. Biases in assignment of participants to groups can cause issues in results of clinical trials. Blinding is another important concept that is used to avoid biases in setting up clinical trials. The level of blinding in a clinical trial indicates which person or party in the clinical trial is exposed to what information. We present examples of different levels of blinding that are supported by the technology disclosed.

Table 1 below presents examples of both randomization and blinding that can be implemented by the technology disclosed.

TABLE 1

Randomization and Blinding in Clinical Trials

| | | Blinding | | |
|---|---|---|---|---|
| Parties | Unblinded | Single Blinded | Double Blinded | Triple Blinded |
| Participant (on Phone) | federated computation randomization | Secure federated computation randomization | Secure federated computation randomization | Secure federated computation randomization |
| Study Team (PI, investigators etc.) | Full data access (if needed) per arm | Full data access (if needed) per arm | Strong crypto based encrypted data but access to only population level stats per arm | Strong crypto based encrypted data but access to only population level stats per arm |
| Monitoring committee | Full data access (if needed) per arm | Full data access (if needed) per arm | Full data access (if needed) per arm | Population level data access (if needed) per arm |
| Data collection server | Full data access (if needed) per arm | Full data access (if needed) per arm | Strong crypto based encrypted data collection | Strong crypto based encrypted data collection |
| Data analysis server/Dashboard | De-identified secure data access | De-identified secure data access | De-identified encrypted data access | De-identified encrypted data access |

TABLE 1-continued

Randomization and Blinding in Clinical Trials

| | | Blinding | | |
|---|---|---|---|---|
| Parties | Unblinded | Single Blinded | Double Blinded | Triple Blinded |
| Unblinded party to send medications vs placebo etc. | N/A | Secure zero-trust data exchange | Secure zero-trust data exchange | Secure zero-trust data exchange |

The four types of privacy techniques presented in Table 1 are explained below:

Unblinded Clinical Trials: In an unblinded or open trial, both the participant and all investigators know to which intervention (placebo vs. real) the participant has been assigned.

Single Blinded Clinical Trials: The definition of a single-blind study is that only the participants are unaware of which intervention they are receiving.

Double Blinded Clinical Trials: In a double blinded study, neither the participants nor the investigators or more specifically the team of investigators responsible for following the participants, collecting data, and assessing outcomes should know the identity of the intervention assignments.

Triple Blinded Clinical Trials: A triple blinded study is an extension of the double blinded design. In such clinical trials, the committee monitoring response variables is not told the identity of the groups. The committee is only given groups level data of participants in the clinical trial.

Completing the description of FIG. 1, the components of the system 100, described above, are all coupled in communication with the network(s) 181. The actual communication path can be point-to-point over public and/or private networks. The communications can occur over a variety of networks, e.g., private networks, VPN, MPLS circuit, or Internet, and can use appropriate application programming interfaces (APIs) and data interchange formats, e.g., Representational State Transfer (REST), JavaScript Object Notation (JSON), Extensible Markup Language (XML), Simple Object Access Protocol (SOAP), Java Message Service (JMS), and/or Java Platform Module System. All of the communications can be encrypted. The communication is generally over a network such as the LAN (local area network), WAN (wide area network), telephone network (Public Switched Telephone Network (PSTN), Session Initiation Protocol (SIP), wireless network, point-to-point network, star network, token ring network, hub network, Internet, inclusive of the mobile Internet, via protocols such as EDGE, 3G, 4G LTE, Wi-Fi and WiMAX. The engines or system components of FIG. 1 are implemented by software running on varying types of computing devices. Example devices are a workstation, a server, a computing cluster, a blade server, and a server farm. Additionally, a variety of authorization and authentication techniques, such as username/password, Open Authorization (OAuth), Kerberos, Secured, digital certificates and more, can be used to secure the communications.

System for Virtual Clinical Trials

Figure 2:
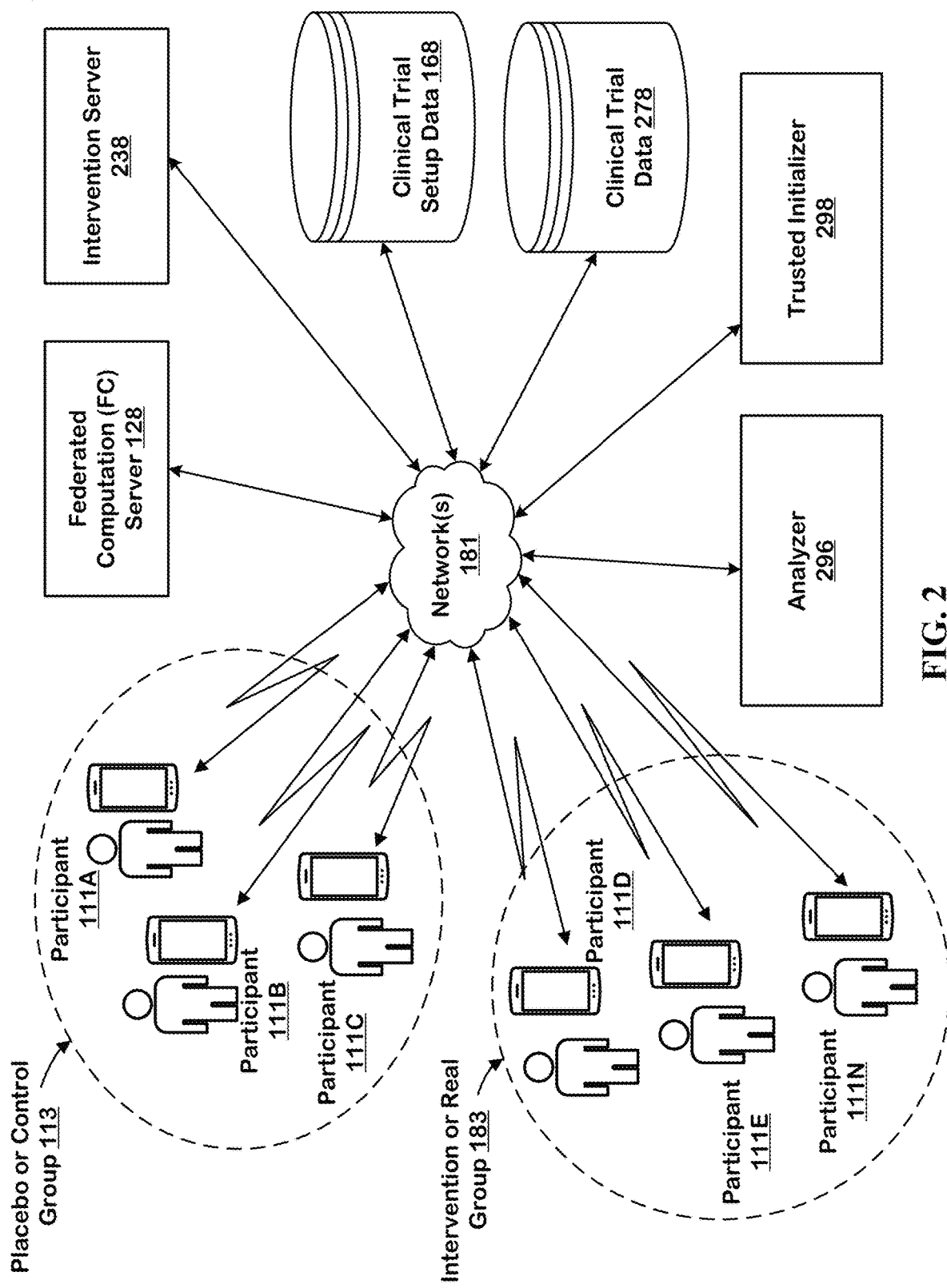
FIG. 2 is an example environment illustrating various parties involved in conducting virtual clinical trials.

FIG. 2 is an example 200 illustrating various parties involved in setting up and execution of the virtual clinical trials. The system includes an intervention server 238, also known as a trusted third-party server. The system includes clinical trials database 278 that can securely store the trial data received from the participants. The data is received in an encrypted form and is stored in encrypted form in the clinical trials database 278. A trusted initializer 298 interacts with the parties during the setup phase to send the correlated randomness known as Beaver triples and a random fixed precision float to FC server and participants. Beaver triples are used to compute secret shared data between the participants and the FC server. An example matrix multiplication technique referred to as "Protocol $\pi_{DMM}$" is presented by De Cock et al. 2020 in their paper titled, "High Performance Logistic Regression for Privacy-Preserving Genome Analysis" available at <<arxiv.org/pdf/2002.05377.pdf>> which is incorporated by reference. An analyzer (or analysis server) 296 can analyze the trial data received from the participants in an encrypted form. The components and databases presented above are connected to each other via the network(s) 181. We now present further details of the components of the system presented above.

Intervention Server or Trusted Third-Party Server

The intervention server 238 (also known as a trusted third-party server) can include logic to implement privacy between the federated computation (FC) server and participants to setup and conduct the clinical trials in a blinded manner. The intervention server generates and stores the public-private key pairs ($pub_{choices}$, and $priv_{choices}$) which are used to encrypt the choice of the intervention i.e., real (or intervention) or placebo (or control). The intervention server can share $pub_{choices}$ key with FC server to assign participants to intervention groups in a blinded manner. The FC server uses $pub_{choices}$ key to encrypt the participants assignment decision. A probability threshold is used to determine how many participants should get assigned to each group (intervention, and placebo). Before sharing the encrypted assignments with the participants, the FC server can generate a random initialization vector (or IV) for each participant and concatenate the bytes to the assignment i where the value of i indicate the number of intervention groups in the clinical trial.

Trusted Initializer

The trusted initializer 298 interacts with FC server and participants during the initialization phase of the virtual clinical trial. The trusted initializer can distribute Beaver triples to both FC server and participants to perform multiplications over data splits in shares. It can also distribute randomization float to both FC server and participants to randomly assign participants to intervention groups. The trusted initializer can also handle other crypto initializations for other multi-part computation protocols.

The technology disclosed can include other implementations in which the trusted initializer is not used. If a trusted initializer is not desired, it is possible to implement the technology disclosed in which the parties compute the correlated data themselves during the setup phase. The idea is to use the homomorphic properties of the Pailler's encryption scheme. Further details of substituting trusted initializer are presented by De Cock et al. 2015 in their paper titled, "Fast, Privacy Preserving Linear Regression over Distributed Datasets based on Pre-Distributed Data" available at <<faculty.washington.edu/mdecock/papers/mdecock2015a.pdf>> which is incorporated by reference. We present three alternative solutions in which the trusted initializer can be removed.

Alternative Implementations without Trusted Initializer

Oblivious Transfer: In this implementation, the participant and the FC server can jointly compute a Diffie Hellman-like protocol to generate a symmetric key choice. The server does not know what key the participant has but can compute every key that the participant could have chosen. The FC server can then encrypt each drug/placebo choice with a different key and send the encryptions to the participant. The participant can only generate one key and thus will only be able to decrypt one of the choices. This keeps the server blind to the participant's choice. By encrypting all drug and placebo choices with the intervention server's $pub_{choice}$ key, we keep the participant blind as well. For further details please see https://www.cs.cmu.edu/~goyal/s18/15503/scribe notes/lecture25.pdf.

Trusted Execution Environment: In this implementation, the technology disclosed can wrap a computation for group assignment on the FC server in a trusted execution environment (TEE) such that the FC server cannot see the computations. This would allow the system to return an encrypted result that is encrypted using the participants key. This keeps the server blind to the result and the participant can similarly decrypt the result, which returns an encrypted selection, keeping the participant blind as well.

Homomorphic Encryption: In this implementation, we can use a different cryptographic building block for the selection algorithm. Instead of using a comparison over secret shares ($\pi_{DC}$), alternatively the system can use $\pi_{HE}$ as presented by Bourse et al. 2019 in the paper titled, "Improved Secure Integer Comparison via Homomorphic Encryption", available at <<eprint.iacr.org/2019/427.pdf>> which is incorporated by reference. This method does not require a trusted initializer from the original algorithm but makes the computations slower since homomorphic encryption (HE) is computationally expensive.

Analyzer or Analysis Server

The analyzer or analysis server 296 can generate and store public-private key pairs $pub_{data}$, and $priv_{data}$. The analysis server can be hosted by the same party which hosts the federated computation (FC) server or as a separate server. The public-private key pairs $pub_{data}$, and $priv_{data}$ can be used to encrypt the clinical trial data from the participants at the end of the trial for transmission and storage in the clinical trial database 278. The data can be decrypted by the party authorized to perform statistical analysis. In one implementation, the encrypted data is stored in a secured and encrypted database. When the principal investigator requires the data for analysis, the system can de-identify the trial data by removing patient identifiers etc. The data is then stored in a database that has restricted access to only authorized persons for performing analysis. In another implementation, the decrypted data can be unblinded, i.e., the principal investigator or the analyst can know which participant belonged to which intervention group (such as real or placebo).

In another implementation, the system can use per user key to encrypt and decrypt the data. In this implementation, the system does not require public-private key pairs $pub_{data}$, and $priv_{data}$ for encrypting the data.

We now present interaction between parties (or servers) presented in FIGS. 1 and 2 to illustrate the initialization phase and setup and participant selection phases of the virtual clinical trial. We also present the interaction between parties after the completion of the virtual clinical trial to analyze data.

Initialization Phase

Figure 3A:
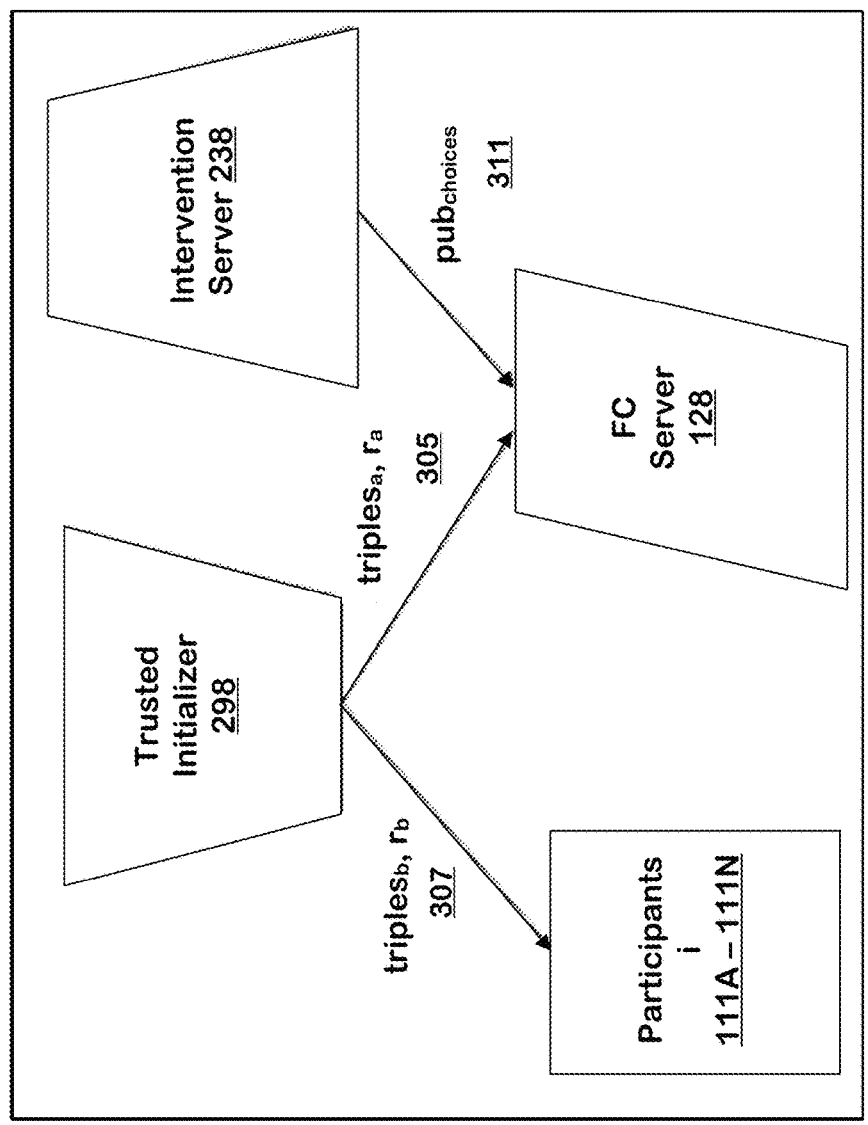
FIG. 3A presents a high-level interaction between various parties during the initialization phase of the virtual clinical trial.

FIG. 3A presents a high-level interaction 300 between various parties during the initialization phase of the virtual clinical trial. The parties involved in the initialization phase include participants 111A-111N, federated computation (FC) server 128, intervention server 238 and trusted initializer 298. The trusted initializer sends the Beaver triples and random fixed precision float r to participants and FC server. The trusted initializer generates a random float with a value between 0 and 1 or [0, 1], converts the random float to a fix precision and generates secret shares ($r_a$, $r_b$). The trusted initializer bit decomposes the shares and sends shares $r_a$ to the FC server and shares $r_b$ to the participants. The third-party or intervention server 238 sends the public key $pub_{choices}$ to the FC server which can use this public key to encrypt the participant assignment decision to an intervention group which can be a real or a placebo group.

Figure 3B:
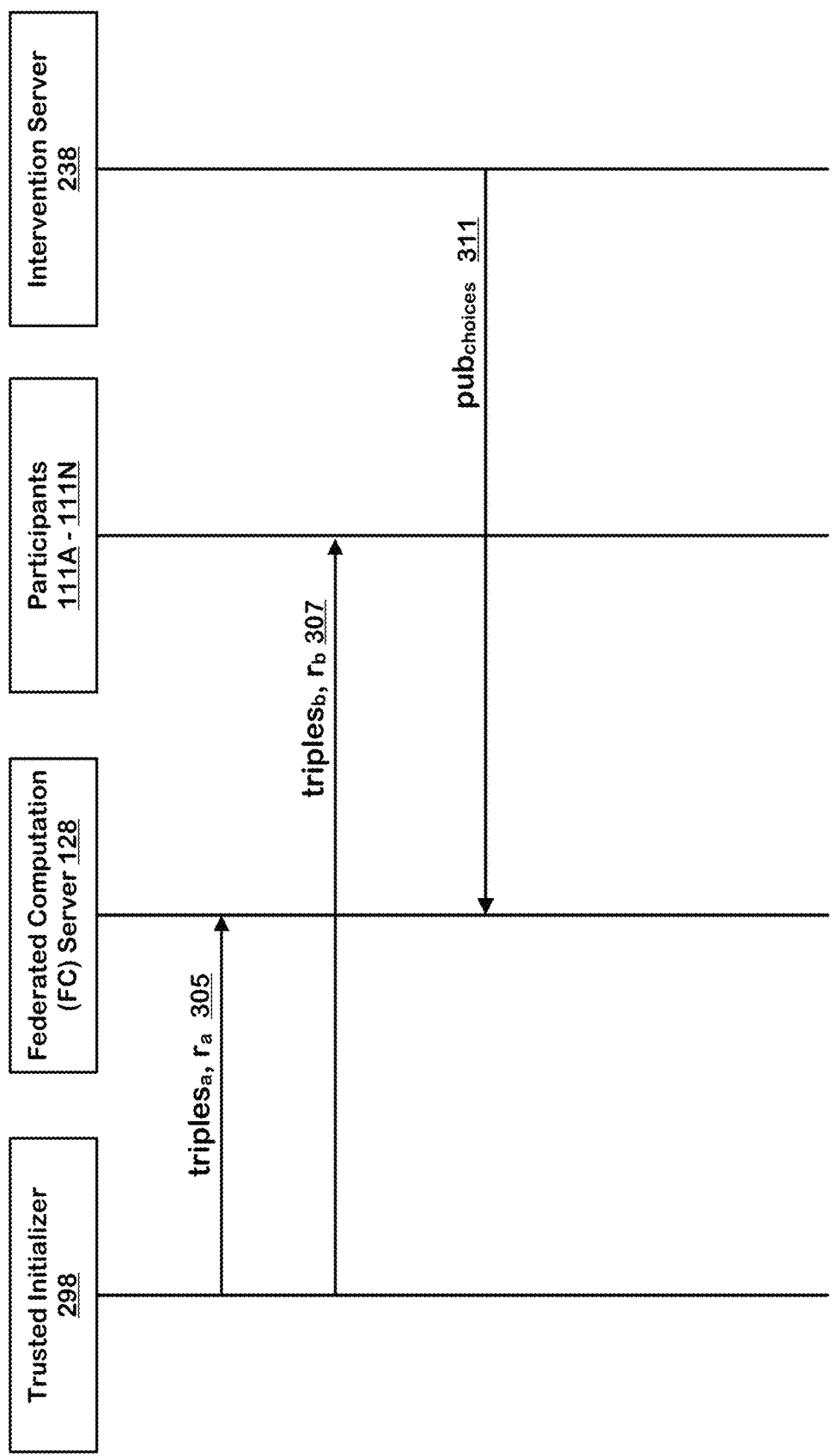
FIG. 3B is a message sequence diagram illustrating message exchanges during initialization phase of the virtual clinical trial.

FIG. 3B presents a message sequence diagram 340 illustrating message exchanges between the various parties during the initialization phase. The process of initialization starts when the trusted initializer 298 sends the secret shares $r_a$ and $triples_a$ to FC server in a message 305. The trusted initializer 298 sends secret shares $r_b$ and $triples_b$ to each participant (111A-111N) in a message 307. The intervention server 238 sends the public key $pub_{choices}$ to the FC server in a message 311. After the initialization process is complete, the setup phase starts. We now present the details of the setup phase including the data transfer between different parties during this phase.

Setup and Participant Selection Phases

Figure 4A:
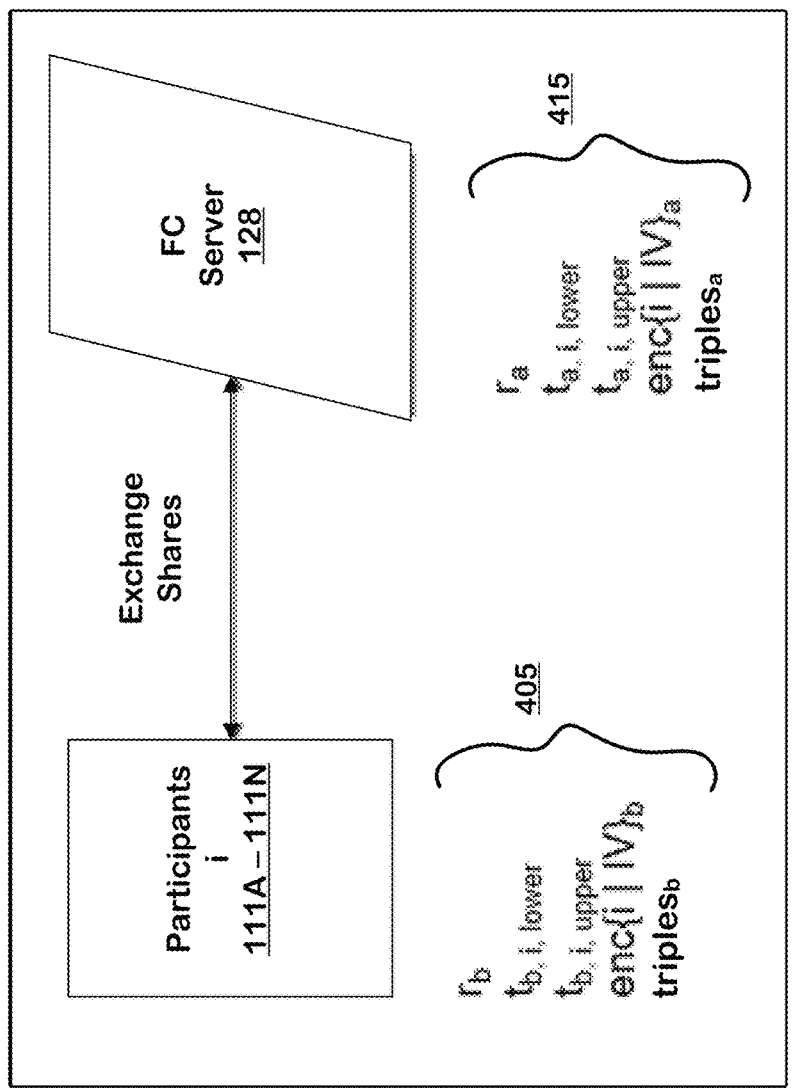
FIG. 4A illustrates exchange of secret shares between participants and federated computation (FC) server during setup phase of virtual clinical trial.

FIG. 4A presents a high-level overview of the exchange of secret shares between the participants and the FC server. The FC server uses the public key $pub_{choices}$ to encrypt the participants' assignment decision. A probability threshold "t" is used to determine how many participants should be assigned to real (or intervention) group and how many participants should be assigned to placebo (or control) group. If there are more than two groups in the trial, probability threshold for each group is used determine if assignment of participants to groups is according to the parameters set by the principal investigator or researcher. The FC server generates a random initialization vector (IV) for each participant before sharing the encrypted assignment to respective participants. The bytes for random IV vector for each participant are concatenated to the assignment i, whereas i represents the choice of a participant receiving a placebo or a drug.

We present an overview of the first phase in this paragraph as presented in illustration 400 in FIG. 4A. The random initialization vector (IV) can add an additional layer of security by adding randomness to the encryption of trial assignments with IV (initialization vector) to prevent any data leakage even when the edge devices are attacked in a security breach. The FC server receives public key $pub_{choices}$ from the intervention server and encrypts all drug and placebo options in the clinical trial with a concatenated IV (represented as enc{i|IV}) for each participant. The IV can prevent collusion between participants so that two users belonging to the same intervention arm (or group) cannot know if they belong to the same arm, even in case of an attack that reveals encrypted assignments. The FC server can generate secret shares for the encrypted assignment choices enc{i I|IV}$_a$ and enc{i|IV}$_b$. It can also generate secret shares of threshold or probability for that given drug or placebo option ($t_{a, i, upper}$, $t_{b, i, upper}$) ($t_{a, i, lower}$, $t_{b, i lower}$). The FC server keeps the "a" secret shares and sends the "b" secret shares to the participants as shown in FIG. 4A.

Figure 4B:
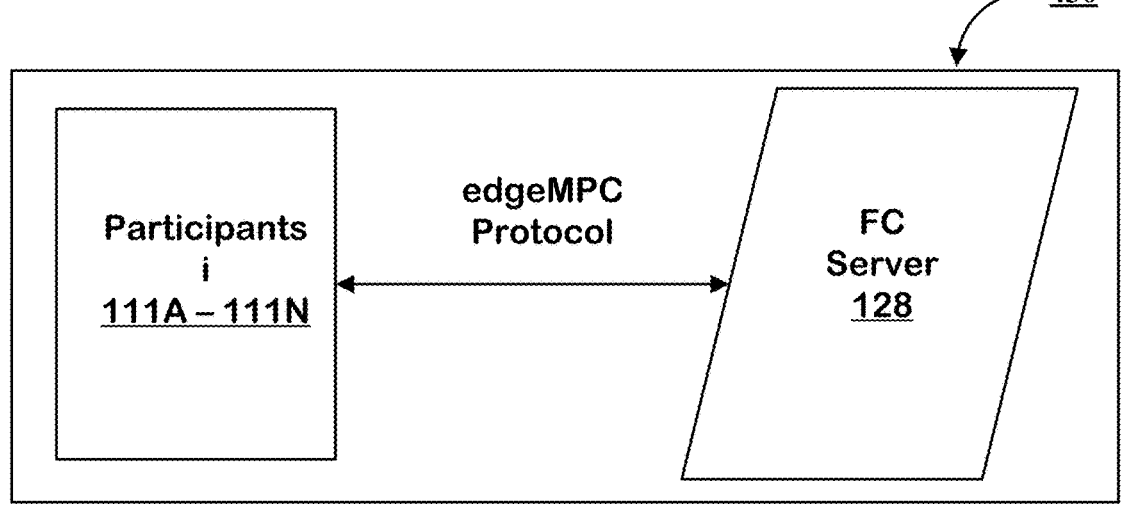
FIG. 4B illustrates high-level interaction between participants and FC server to compute secrets and combine secrets during selection phase of virtual clinical trial.
Figure 4B:
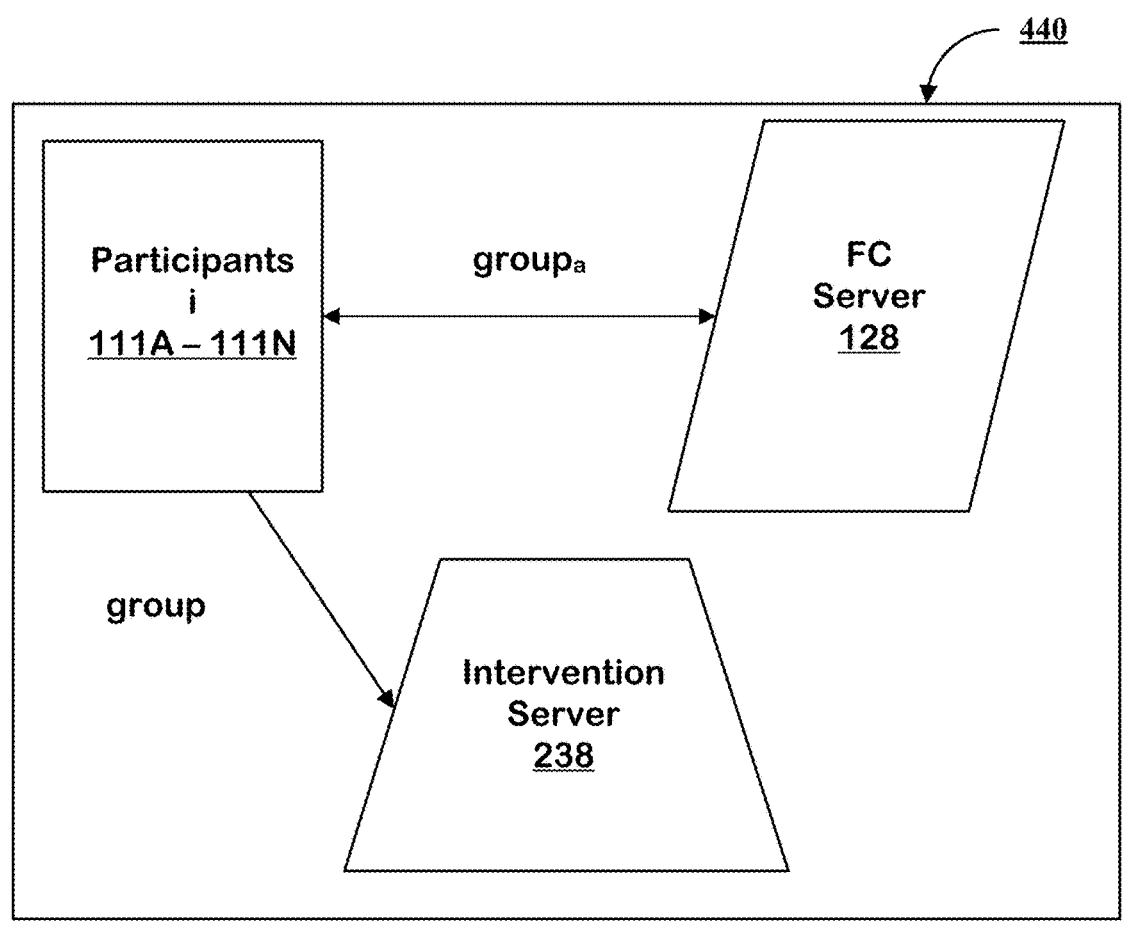

The setup phase can be partitioned into two steps. In the first step all parties (participants and FC server) use their secret shares to perform computations in parallel. In the second step the computed results from the FC server are sent to participants to combine with results at the participant side to generate the encrypted values of assignments. FIG. 4B presents a high-level illustration 430 of the first step of selection phase and a high-level illustration 440 of the second step of the selection phase of the virtual clinical trial. In the first step, the parties use multi-party computation (MPC) protocol to perform computations in parallel. When the results are generated at all parties, the FC server sends the computed group assignment on its end (group$_a$) to participants.

The participants can combine the group assignment from FC server with their own computed results to generate their respective group assignment (group). Note that the assignments including the secret shares parts of the assignments are encrypted using the public key pub$_{choices}$ from a third-party server or an intervention server. Therefore, no party (i.e., participants or FC server) can know the assignment of a participant to a group. The participants can send their encrypted group assignment to the intervention server which can use the private key priv$_{choices}$ to decrypt and identify the assignment of participants to groups. The intervention server can use these results to determine whether the assignments fulfil the threshold requirements for assignments of participants to groups required by the principal investigator. The intervention server can also use these assignments of participants to distribute correct intervention (real drugs or placebo) to participants based on their assignment.

Figure 4C:
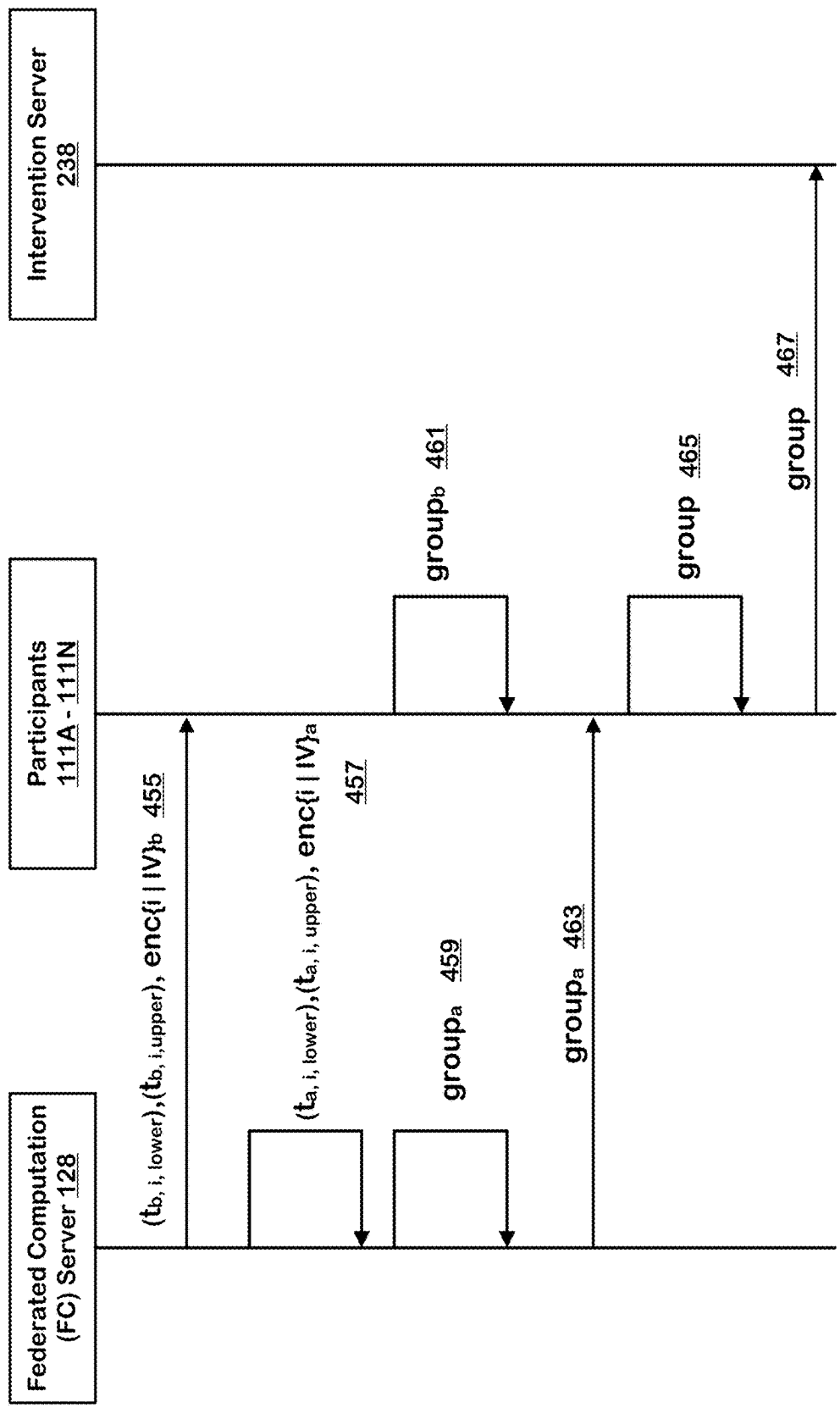
FIG. 4C is a message sequence diagram illustrating message exchanges during setup and participant selection phases.

FIG. 4C presents a message sequence diagram 450 illustrating the messages exchanged between FC server, participants and intervention server during setup and participant selection phases. The setup process starts when the FC sever sends the "b" secret shares for upper and lower boundaries of threshold or probabilities for assignment of participants to each group in the virtual clinical trial i.e., ($t_{b, i, lower}$), ($t_{b, i, upper}$). The FC server also sends the "b" shares of encrypted assignment choice i.e., enc{i|IV}$_b$ for each group i in the clinical trial. Each option choice is concatenated with an initialization vector (IV) for security purposes. The message 455 from the FC server to each participant includes the above listed data.

The FC server keeps the "a" secret shares of assignment data for performing its part of multi-party computations. This is shown as ($t_{a, i, lower}$), ($t_{a, i, upper}$), enc{i|IV}$_a$ and labeled as a message 457. The server and the participants perform computations with their respective data and produce "a" and "b" parts of the group assignment of participants as shown in messages 459 and 461 respectively. One implementation of the multi-party computation (MPC) protocols referenced and used in the following algorithm are disclosed in De Cock et al. 2020 and incorporated by reference, and by De Cock et al. 2017 in their paper titled "Efficient and Private Scoring of Decision Trees, Support Vector Machines and Logistic Regression Models based on Pre-Computation", available at <<eprint.iacr.org/2016/736.pdf>> which is incorporated by reference. These MPC protocols are used as building blocks for the selection algorithm. We provide details of the selection algorithm below. There are two high-level steps (Step A and Step B) in the selection algorithm. Step B further comprises of substeps (i) to (v).

Selection Algorithm in a Virtual Clinical Trial

Step A: Let i ∈C where C is the set of drug and placebo options and i is the specific drug and its upper (inclusive) and lower (exclusive) thresholds. For example, consider a clinical trial with three groups, two using real drug and one group using a placebo. One example selection threshold values of participants to these groups is given as C={(drugA, $t_{drugA, lower}$=0, $t_{drugA, upper}$=0.33), (drugB, $t_{drugB, lower}$=0.33, $t_{drugB, upper}$=0.66), (placebo, $t_{placebo, lower}$=0.66, $t_{placebo, upper}$=1)}.

Step B: Compute the following for each participant and corresponding server shares $\Sigma_i \pi_{DMM}(\pi_{DMM}(\pi_{DC}(r, t_{i, lower})$, $\pi_{xor}(\pi_{DC}(r, t_{i, upper}), 1))$, enc{i|IV}). The following substeps (i) to (v) provide a breakdown of the individual operations in the formula above:

Substep (i): $\pi_{DC}(r, t_{i, lower})$ returns 1 if r>=$t_{i, lower}$ else 0.

The inputs to function in substep (i) are secret shares so that no party can know the value of inputs. At the end of the protocol, the result will be a secret share version of 1 or 0 if r>=$t_{i, lower}$. This function is used to test thresholds, and determine which drug group a participant is in. Because this function only performs ">=" i.e., "greater than or equals to" comparison and we want to know if the value is in the range ($t_{i, lower}$, $t_{i, upper}$), we apply the next substep to determine this.

Substep (ii): $\pi_{XOR}$(Value, 1) Returns the XOR of the Value and 1.

The inputs to this function are secret share values. The value "1" is also secret share between all parties performing the calculation. The protocol will return two values xor'd with each other; in this case, "value" xor'd with "1". We apply this protocol because $\pi_{DC}$ returns ">=" comparison and we need a "<" comparison. This XOR operation will flip the value returned by $\pi_{DC}$ essentially flipping comparison made.

Note, "1" is the actual value but all inputs are secret shares so it will need to be secret shared between the parties participating in the protocol. In this case, a valid sharing with two parties would be "1" and "0". When performing this substep, the participant will input 0 and the FC server will input 1.

Substep (iii): $\pi_{DMM}(\pi_{DC}(r, t_{i, lower})$, $\pi_{xor}(\pi_{DC}(r, t_{i, upper})$, 1))<–Returns 1 if $t_{i, upper}$>r>=$t_{i, lower}$ Otherwise 0.

The inputs to above function are secret shares and the output will be secret share as well. $\pi_{DMM}$(value1, value2) returns the secret share multiplication of "value1" and "value2". Since $\pi_{DC}(r, t_{i, lower})$ returns 1 if r>=$t_{i, lower}$ and $\pi_{xor}(\pi_{DC}(r, t_{i, upper})$, 1) returns 1 if r<$t_{i, upper}$ then $\pi_{DMM}(\pi_{DC}(r, t_{i, lower})$, $\pi_{xor}(\pi_{DC}(r, t_{i, upper})$, 1)) return 1 if $t_{i, upper}$>r>=$t_{i, lower}$. This is because the multiplication will always return secret share 0 if any value is 0 (anything times 0 is 0) so this will only return 1 when r is in that range.

Substep (iv): $\pi_{DMM}(\pi_{DMM}(\pi_{DC}(r, t_{i, lower})$,$\pi_{xor}(\pi_{DC}(r, t_{i, upper})$, 1)), Enc{i|IV})<–Returns Enc{i|IV} if $t_{i, upper}$>r>=$t_{i, lower}$ Otherwise 0.

The inputs of these functions are all secret share values and the output will also be a secret share. Since the previous section returns 1 if and only if r is $t_{i, upper}$>r>=$t_{i, lower}$, then this function will return enc{i|IV} if and only if $t_{i, upper}$>r>=$t_{i, lower}$ (it either returns 1*enc{i|IV} or 0*enc{i|IV} depending on r and the thresholds).

Substep (v): $\Sigma_i \pi_{DMM}(\pi_{DMM}(\pi_{DC}(r, t_{i, lower})$,$\pi_{xor}(\pi_{DC}(r, t_{i, upper})$, 1)), Enc{i|IV}) Return the Selected Enc{i|IV} for the Group which the Following Statement Holds True: $t_{i, upper}$>r>=$t_{i, lower}$.

Since the previous protocol returns 0 or enc{i|IV} then this complete protocol returns enc{i|IV} for the i where r was between the thresholds. This is because r will only be between one set of thresholds, which means only 1 value will not be secret share i.e., "0". Summing everything we sum 0 plus the selected enc{i|IV}.

At the end of the above algorithm, the server and the client or edge devices of participants have the result of the above computation for their corresponding shares. One implementation of the computations for Secure Distributed Matrix Multiplication protocol $\pi_{DMM}$ are disclosed in De Cock et al. 2020 and incorporated by reference. One implementation of the computations for Secure Distributed Comparison Protocol $\pi_{DC}$ are disclosed in De Cock et al. 2017 in their paper titled "Efficient and Private Scoring of Decision Trees, Support Vector Machines and Logistic Regression Models based on Pre-Computation" which is incorporated by reference. One implementation of the computations for Exclusive OR (XOR) Protocol $\pi_{xor}$ for Upper Threshold Comparison are disclosed in De Cock et al. 2020 and incorporated by reference. One implementation of secure bit decomposition for generating secret shares is disclosed in De Cock et al. 2020 and incorporated by reference. One implementation of converting decomposed bit to secret shared integer is disclosed in De Cock et al. 2020 in their paper listed above and incorporated by reference.

Referring to the sequence diagram in FIG. 4B, the FC server sends result of the above algorithm to the participants. The participant adds the two shares to get the final selection (step 465). The value will be enc{i IV} depending on r, $t_{i, lower}$ and $t_{i, upper}$. Each Participant is blinded because $pub_{choices}$ is never shared, so the participant has no way of knowing what this value means. FC server does not have access to the encrypted group assignments from participants and therefore, it remains blinded to assignment of participants to groups. Hence, privacy or blinding is maintained when assigning participants to groups by applying the above selection algorithm. The participants can send their encrypted group assignments to intervention server which can decrypt and see the group assignment of participants. The intervention server can then compare the assignment ratio requirements for the clinical trial with the actual assignments of participants to see if it meets the requirements set by the researcher. If the assignment does not meet the requirements, then the above selection process is repeated to generate another random assignment of participants to groups. At the end of the clinical trial, the applications executing on devices of participants can send trial data in encrypted form to the analyzer or the analysis server. We present the details of how the trial data is sent to the analyzer in the following section.

Trial Data Analysis Phase

Figure 5A:
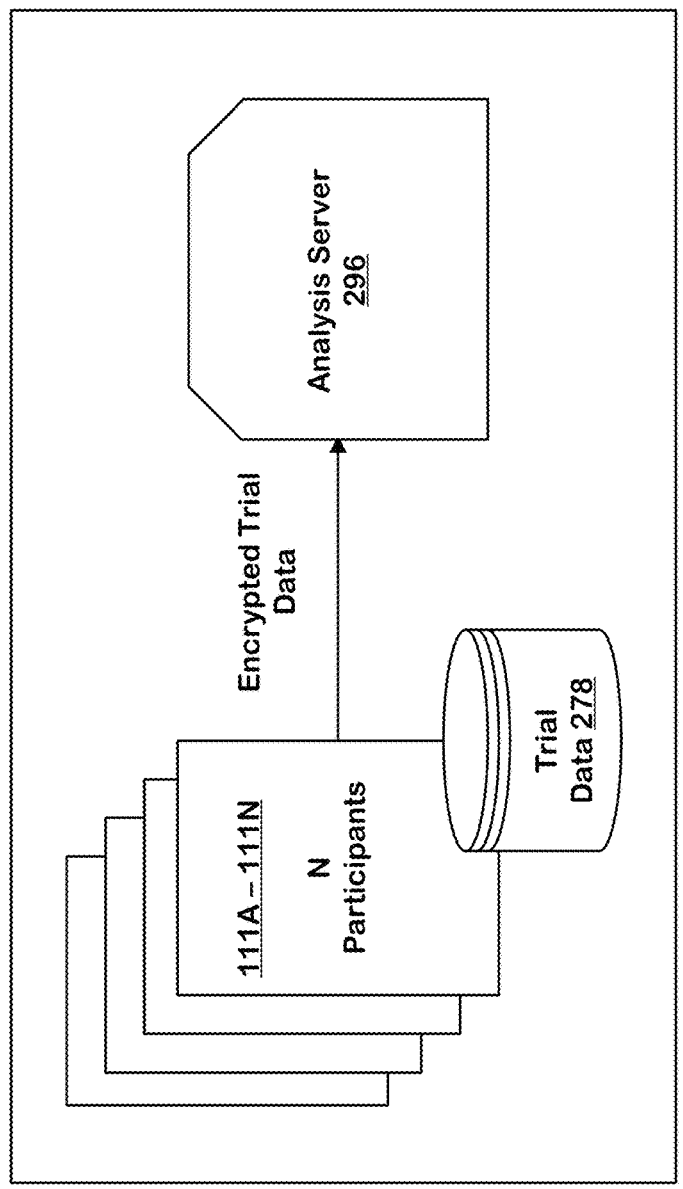
FIG. 5A illustrates a high-level interaction between participants and analysis server for trial data analysis.

FIG. 5 presents an illustration 500 in which the participants 111A-111N send their respective trial data collected via the app running on their mobile devices or other wearable devices to the analysis server 296. The trial data from the participants can be stored in a trial database 278 in an encrypted form. The trial data is encrypted using the public key from the analysis server ($pub_{data}$). The analysis server can therefore decrypt the trial data using private key ($priv_{data}$) and analyze the decrypted data. The message communication between the participants and the analysis server to collect the trial data is presented below.

Figure 5B:
FIG. 5B is a message sequence diagram illustrating message exchanges after completion of the clinical trial to collect encrypted data from participants for storage and analysis.

FIG. 5B presents a message sequence diagram 550 that illustrates message exchanges between participants and the analyzer (or analysis server). The process starts when the apps executing on edge devices such as mobile, portable or wearable devices have collected trial data of respective participants. The edge devices of participants 111A-111N send a message 555 to analyzer 296 that the clinical trial has completed. In one implementation, the analyzer 296 can wait until it receives a trial complete message from edge devices of all participants in the clinical trial before sending a public key $pub_{data}$ to edge devices of participants to encrypt the trial data (message 557). The edge devices of participants can encrypt the trial data using the public key $pub_{data}$ of the analyzer (or the analysis server) 296 (message 559). The encrypted trial data from edge devices of participants is sent to the analysis server via the message 561.

Triple Blinded Clinical Trials

The technology disclosed can be used to conduct a triple blinded clinical trial. In a triple blinded clinical trial, the committee monitoring the response variables is not told the identity of the groups. The committee is only given group level data of participants in the clinical trial. In one implementation, the technology disclosed can implement blinding between participants and the monitoring committee by aggregating the collected data from each group in the clinical trial for each feature. The aggregated data is encrypted using public key $pub_{data}$ of the third-party analysis server. The encrypted aggregated group level data is then transmitted to the analysis server. The analysis server can decrypt the aggregated data using private key $priv_{data}$. The decrypted aggregated data per group can be accessed by the monitoring committee for analysis. Note that the monitoring committee does not have access to individuals' raw data collected throughout the trial nor have knowledge of the treatment arms and is therefore blinded. It can only access the aggregated data that is at the population level.

PARTICULAR IMPLEMENTATIONS

We describe various implementations of a system for conducting virtual or decentralized clinical trials.

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

A system implementation of the technology disclosed includes one or more processors coupled to memory. The memory can be loaded with instructions to randomly assign participants of a clinical trial to treatment and placebo groups in a blinded manner. The system can be loaded from either a transitory or a non-transitory computer readable storage medium. The system comprises of a federate server configured with group assignability data specifying a plurality of groups assignable to participants in a clinical trial. The federated server is also configured with group distribution data specifying distribution of the participants into groups in the plurality of groups. The plurality of groups can include at least one placebo group and one or more treatment groups.

The system comprises an intervention server configured to generate group encryption keys for encrypting the group assignability data. The group encryption keys include a public key and a private key. The federated server is configured to generate group distribution thresholds for each of the groups based on the group distribution data to encrypt the group assignability data. The federated server includes logic to use the public key and respective random initialization vectors for each of the participants to generate respective encrypted group assignability data for each of the participants. The federated server can include logic to split the group distribution thresholds into a federated server share of the group distribution thresholds and an edge device share of the group distribution thresholds. The federated server can include logic to split the encrypted group assignability data into a federated server share of the encrypted group assignability data and an edge device share of the encrypted group assignability data. The federated server can include logic to generate respective federated server assignments of each of the participants to one of the groups using the federated server share of the group distribution thresholds and the federated server share of the encrypted group assignability data.

The respective edge devices of each of the participants are in communication with the federated server. The edge devices can be configured to generate respective edge device assignments of each of the participants to one of the groups using the edge device share of the group distribution thresholds and the edge device share of the encrypted group assignability data. The edge devices include the logic to respectively combine the federated server assignments and the edge device assignments to produce respective encrypted group assignments of each of the participants to one of the groups.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

In one implementation, the system can comprise an initializer server in communication with the federated server and the respective edge devices. The initializer server can be configured to generate Beaver multiplication triples and respective random floating-point numbers for each of the participants. The random floating-point numbers can be between zero and one. The initializer server can be further configured to convert the random floating-point numbers into random fixed-precision numbers.

The initializer server can be configured with bit decomposition protocol to split the Beaver multiplication triples into a federated server share of the Beaver multiplication triples and an edge device share of the Beaver multiplication triples.

The initializer server can be further configured with bit decomposition protocol to split the random fixed-precision numbers into a federated server share of the random fixed-precision numbers and an edge device share of the random fixed-precision numbers.

The initializer server can be configured to deliver the federated server share of the Beaver multiplication triples to the federated server. The initializer server can deliver the edge device share of the Beaver multiplication triples to the respective edge devices.

The initializer server can be configured to deliver the federated server share of the random fixed-precision numbers to the federated server. The initializer server can deliver the edge device share of the random fixed-precision numbers to the respective edge devices.

The federated server can be configured to generate the federated server assignments using the federated server share of the Beaver multiplication triples and the federated server share of the random fixed-precision numbers.

The respective edge devices can be configured to generate the edge device assignments using the edge device share of the Beaver multiplication triples and the edge device share of the random fixed-precision numbers.

Each of the group distribution thresholds can include an upper distribution bound and a lower distribution bound.

The federated server can include logic to convert, for each of the groups, the upper distribution bound into an upper bound fixed-precision number, and the lower distribution bound into a lower bound fixed-precision number.

The federated server can be configured with bit decomposition protocol to split, for each of the groups, the upper bound fixed-precision number into a first part of the upper bound fixed-precision number and a second part of the upper bound fixed-precision number.

The federated server can be configured with bit decomposition protocol to split, for each of the groups, the lower bound fixed-precision number into a first part of the lower bound fixed-precision number and a second part of the lower bound fixed-precision number.

The federated server can be configured to generate, for each of the groups, the federated server share of the group distribution thresholds using the first part of the upper bound fixed-precision number and the first part of the lower bound fixed-precision number. The federated server can be further configured to generate, for each of the groups, the edge device share of the group distribution thresholds using the second part of the upper bound fixed-precision number and the second part of the lower bound fixed-precision number.

The intervention server is in communication with the respective edge devices. The intervention server can be further configured to receive the encrypted group assignments from the respective edge devices, and to decrypt the encrypted group assignments using the private key to determine respective group assignments of each of the participants.

The intervention server can be further configured to determine, based on the group assignments, whether the distribution of the participants into the groups, as specified by the group distribution data, is met or not.

The intervention server can be further configured to cause the federated server and the respective edge devices to respectively regenerate the federated server assignments and the edge device assignments to reproduce the encrypted group assignments when the distribution is not met.

The federated server can be further configured to apply a secure distributed matrix multiplication protocol ($\pi_{DMM}$), a secure distributed comparison protocol ($\pi_{DC}$), and an exclusive-or protocol (xor) on the federated server share of the group distribution thresholds, the federated server share of the encrypted group assignability data, the federated server share of the Beaver multiplication triples, and the federated server share of the random fixed-precision numbers to generate the federated server assignments.

The respective edge devices can be further configured to apply the secure distributed matrix multiplication protocol ($\pi_{DMM}$), the secure distributed comparison protocol ($\pi_{DC}$), and the exclusive-or protocol (xor) on the edge device share of the group distribution thresholds, the edge device share of the encrypted group assignability data, the edge device share of the Beaver multiplication triples, and the edge device share of the random fixed-precision numbers to generate the edge device assignments.

The intervention server can be further configured to deliver the group assignability data, the group distribution data, and the public key to the federated server over a secure communication channel.

The federated server can be further configured to deliver the federated server assignments to the respective edge devices over a secure communication channel.

In one implementation, the system can further comprise an analysis server configured to generate data encryptions keys that include a public key and a private key.

The analysis server can be in communication with the respective edge devices. The analysis server can be further configured to deliver the public key to the respective edge devices.

The respective edge devices can be further configured to encrypt trial data generated by the participants during the clinical trial using the public key to generate encrypted trial data, and to deliver the encrypted trial data to the analysis server.

The analysis server can be further configured to use the private key to decrypt the encrypted trial data to access the trial data, and to determine an outcome of the clinical trial based on the trial data.

The intervention server can be further configured to collect the trial data on a group-by-group basis and aggregate the collected trial data. The intervention server can encrypt the aggregated trial data using the public key, and deliver the encrypted aggregated trial data to the analysis server.

The analysis server can be further configured to use the private key to decrypt the encrypted aggregated trial data to access the aggregated trial data. The analysis server can include logic to determine an outcome of the clinical trial based on the aggregated trial data.

Other implementations consistent with this system may include a non-transitory computer readable storage medium storing instructions executable by a processor to perform functions of the system described above. Yet another implementation may include a method performing the functions of the system described above.

Aspects of the technology disclosed can be practiced as a method of conducting blinded clinical trials. The method can include receiving group assignability data specifying a plurality of groups assignable to participants in a clinical trial, and group distribution data specifying distribution of the participants into groups in the plurality of groups. The groups can include at least one placebo group and one or more treatment groups. The method can include generating group encryption keys for encrypting the group assignability data. The group encryption keys can include a public key and a private key. The method can include generating respective group distribution thresholds for each of the groups based on the group distribution data. The method can include encrypting the group assignability data using the public key and respective random initialization vectors for each of the participants to generate respective encrypted group assignability data for each of the participants. The method can include splitting the group distribution thresholds into a federated server share of the group distribution thresholds and an edge device share of the group distribution thresholds. The method can include splitting the encrypted group assignability data into a federated server share of the encrypted group assignability data and an edge device share of the encrypted group assignability data. The method can include generating respective federated server assignments of each of the participants to one of the groups using the federated server share of the group distribution thresholds and the federated server share of the encrypted group assignability data. The method can include using the respective edge devices of each of the participants to generate respective edge device assignments of each of the participants to one of the groups using the edge device share of the group distribution thresholds and the edge device share of the encrypted group assignability data. The respective edge devices can be in communication with the federated server. The method can include respectively combining the federated server assignments and the edge device assignments to produce respective encrypted group assignments of each of the participants to one of the groups.

This method implementation can incorporate any of the features of the system described immediately above or throughout this application that apply to the method implemented by the system. In the interest of conciseness, alternative combinations of method features are not individually enumerated. Features applicable to systems, methods, and articles of manufacture are not repeated for each statutory class set of base features. The reader will understand how features identified in this section for one statutory class can readily be combined with base features in other statutory classes.

Other implementations consistent with this method may include a non-transitory computer readable storage medium storing instructions executable by a processor to perform any of the methods described above. Yet another implementation may include a system with memory loaded from a computer readable storage medium with program instructions to perform the method described above. The system can be loaded from either a transitory or a non-transitory computer readable storage medium.

As an article of manufacture, rather than a method, a non-transitory computer readable medium (CRM) can be loaded with program instructions executable by a processor. The program instructions when executed, implement the computer-implemented method described above. Alternatively, the program instructions can be loaded on a non-transitory CRM and, when combined with appropriate hardware, become a component of one or more of the computer-implemented systems that practice the method disclosed.

Each of the features discussed in this particular implementation section for the method implementation apply equally to CRM implementation. As indicated above, all the method features are not repeated here, in the interest of conciseness, and should be considered repeated by reference.

CLAUSES

1. A system, comprising:
a federated server configured with group assignability data specifying a plurality of groups assignable to participants in a clinical trial, and group distribution data specifying distribution of the participants into groups in the plurality of groups, the groups including at least one placebo group and one or more treatment groups;
an intervention server configured to generate group encryption keys for encrypting the group assignability data, the group encryption keys including a public key and a private key;
the federated server configured to generate respective group distribution thresholds for each of the groups based on the group distribution data, to encrypt the group assignability data using the public key and respective random initialization vectors for each of the participants to generate respective encrypted group assignability data for each of the participants, to split the group distribution thresholds into a federated server share of the group distribution thresholds and an edge device share of the group distribution thresholds, to split the encrypted group assignability data into a federated server share of the encrypted group assignability data and an edge device share of the encrypted group assignability data, and to generate respective federated server assignments of each of the participants to one of the groups using the federated server share of the group distribution thresholds and the federated server share of the encrypted group assignability data; and respective edge devices of each of the participants, the respective edge devices in communication with the federated server, and configured to generate respective edge device assignments of each of the participants to one of the groups using the edge device share of the group distribution thresholds and the edge device share of the encrypted group assignability data, and to respectively combine the federated server assignments and the edge device assignments to produce respective encrypted group assignments of each of the participants to one of the groups.

2. The system of clause 1, further comprising an initializer server in communication with the federated server and the respective edge devices, and configured to generate Beaver multiplication triples and respective random floating-point numbers for each of the participants.

3. The system of clause 2, wherein the random floating-point numbers are between zero and one.

4. The system of clause 3, wherein the initializer server is further configured to convert the random floating-point numbers into random fixed-precision numbers.

5. The system of clause 2, wherein the initializer server is further configured with bit decomposition protocol to split the Beaver multiplication triples into a federated server share of the Beaver multiplication triples and an edge device share of the Beaver multiplication triples.

6. The system of clause 4, wherein the initializer server is further configured with bit decomposition protocol to split the random fixed-precision numbers into a federated server share of the random fixed-precision numbers and an edge device share of the random fixed-precision numbers.

7. The system of clause 5, wherein the initializer server is further configured to deliver the federated server share of the Beaver multiplication triples to the federated server, and to deliver the edge device share of the Beaver multiplication triples to the respective edge devices.

8. The system of clause 6, wherein the initializer server is further configured to deliver the federated server share of the random fixed-precision numbers to the federated server, and to deliver the edge device share of the random fixed-precision numbers to the respective edge devices.

9. The system of clause 8, wherein the federated server is further configured to generate the federated server assignments using the federated server share of the Beaver multiplication triples and the federated server share of the random fixed-precision numbers.

10. The system of clause 8, wherein the respective edge devices are further configured to generate the edge device assignments using the edge device share of the Beaver multiplication triples and the edge device share of the random fixed-precision numbers.

11. The system of clause 1, wherein each of the group distribution thresholds includes an upper distribution bound and a lower distribution bound.

12. The system of clause 11, wherein the federated server is further configured to convert, for each of the groups, the upper distribution bound into an upper bound fixed-precision number, and the lower distribution bound into a lower bound fixed-precision number.

13. The system of clause 12, wherein the federated server is further configured with bit decomposition protocol to split, for each of the groups, the upper bound fixed-precision number into a first part of the upper bound fixed-precision number and a second part of the upper bound fixed-precision number.

14. The system of clause 13, wherein the federated server is further configured with bit decomposition protocol to split, for each of the groups, the lower bound fixed-precision number into a first part of the lower bound fixed-precision number and a second part of the lower bound fixed-precision number.

15. The system of clause 14, wherein the federated server is further configured to generate, for each of the groups, the federated server share of the group distribution thresholds using the first part of the upper bound fixed-precision number and the first part of the lower bound fixed-precision number and the edge device share of the group distribution thresholds using the second part of the upper bound fixed-precision number and the second part of the lower bound fixed-precision number.

16. The system of clause 1, wherein the intervention server is in communication with the respective edge devices, and further configured to receive the encrypted group assignments from the respective edge devices, and to decrypt the encrypted group assignments using the private key to determine respective group assignments of each of the participants.

17. The system of clause 16, wherein the intervention server is further configured to determine, based on the group assignments, whether the distribution of the participants into the groups, as specified by the group distribution data, is met or not.

18. The system of clause 17, wherein, when the distribution is not met, the intervention server is further configured to cause the federated server and the respective edge devices to respectively regenerate the federated server assignments and the edge device assignments to reproduce the encrypted group assignments.

19. The system of clause 4, wherein the federated server is further configured to apply a secure distributed matrix multiplication protocol ($\pi$DMM), a secure distributed comparison protocol ($\pi$DC), and an exclusive Or protocol (xor) on the federated server share of the group distribution thresholds, the federated server share of the encrypted group assignability data, the federated server share of the Beaver multiplication triples, and the federated server share of the random fixed-precision numbers to generate the federated server assignments.

20. The system of clause 19, wherein the respective edge devices are further configured to apply the secure distributed matrix multiplication protocol ($\pi$DMM), the secure distributed comparison protocol ($\pi$DC), and the exclusive Or protocol (xor) on the edge device share of the group distribution thresholds, the edge device share of the encrypted group assignability data, the edge device share of the Beaver multiplication triples, and the edge device share of the random fixed-precision numbers to generate the edge device assignments.

21. The system of clause 1, wherein the intervention server is further configured to deliver the group assignability data, the group distribution data, and the public key to the federated server over a secure communication channel.
22. The system of clause 1, wherein the federated server is further configured to deliver the federated server assignments to the respective edge devices over a secure communication channel.
23. The system of clause 1, further comprising an analysis server configured to generate data encryptions keys that include a public key and a private key.
24. The system of clause 23, wherein the analysis server is in communication with the respective edge devices, and further configured to deliver the public key to the respective edge devices.
25. The system of clause 24, wherein the respective edge devices are further configured to encrypt trial data generated by the participants during the clinical trial using the public key to generate encrypted trial data, and to deliver the encrypted trial data to the analysis server.
26. The system of clause 25, wherein the analysis server is further configured to use the private key to decrypt the encrypted trial data to access the trial data, and to determine an outcome of the clinical trial based on the trial data.
27. The system of clause 23, wherein the intervention server is further configured to collect the trial data on a group-by-group basis, aggregate the collected trial data, encrypt the aggregated trial data using the public key, and deliver the encrypted aggregated trial data to the analysis server.
28. The system of clause 27, wherein the analysis server is further configured to use the private key to decrypt the encrypted aggregated trial data to access the aggregated trial data, and to determine an outcome of the clinical trial based on the aggregated trial data.

Computer System

Figure 6:
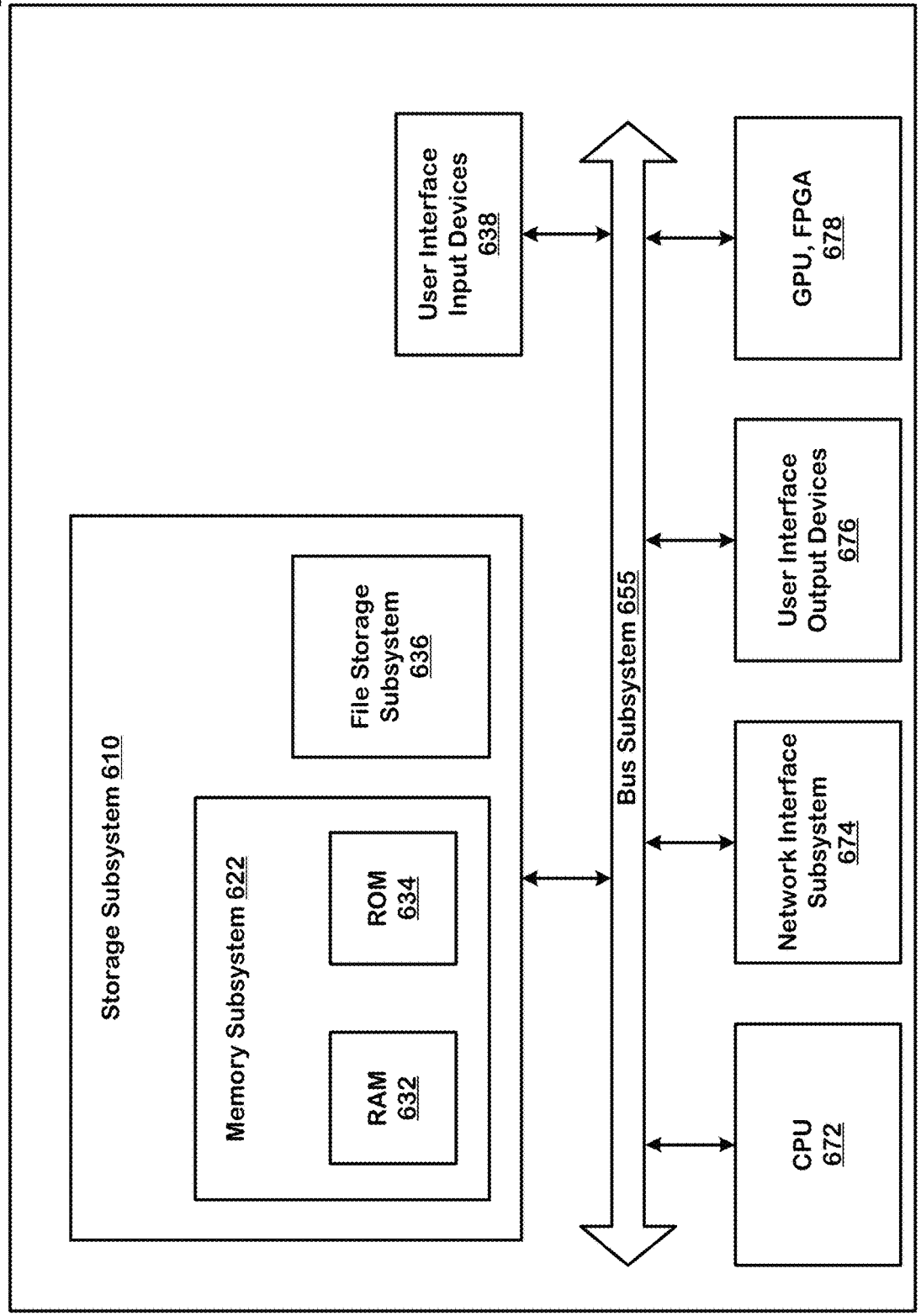
FIG. 6 is a block diagram of a computer system that can be used to implement the system of FIGS. 1 and 2.

FIG. 6 is a simplified block diagram of a computer system 600 that can be used to implement the technology disclosed. Computer system typically includes at least one processor 672 that communicates with a number of peripheral devices via bus subsystem 655. These peripheral devices can include a storage subsystem 610 including, for example, memory subsystem 622 and a file storage subsystem 636, user interface input devices 638, user interface output devices 676, and a network interface subsystem 674. The input and output devices allow user interaction with a computer system. Network interface subsystem provides an interface to outside networks, including an interface to corresponding interface devices in other computer systems.

User interface input devices 638 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into a computer system.

User interface output devices 676 can include a display subsystem, a printer, a fax machine, or non-visual displays such as audio output devices. The display subsystem can include a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from the computer system to the user or to another machine or computer system.

Storage subsystem 610 stores programming and data constructs that provide the functionality of some or all of the modules and methods described herein. These software modules are generally executed by processor alone or in combination with other processors.

Memory used in the storage subsystem can include a number of memories including a main random access memory (RAM) 632 for storage of instructions and data during program execution and a read only memory (ROM) 634 in which fixed instructions are stored. The file storage subsystem 636 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem in the storage subsystem, or in other machines accessible by the processor.

Bus subsystem 655 provides a mechanism for letting the various components and subsystems of a computer system communicate with each other as intended. Although a bus subsystem is shown schematically as a single bus, alternative implementations of the bus subsystem can use multiple busses.

Computer system itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of the computer system depicted in FIG. 6 is intended only as a specific example for purposes of illustrating the technology disclosed. Many other configurations of the computer system are possible having more or less components than the computer system depicted in FIG. 6.

The computer system 600 includes GPUs or FPGAs 678. It can also include machine learning processors hosted by machine learning cloud platforms such as Google Cloud Platform, Xilinx, and Cirrascale. Examples of deep learning processors include Google's Tensor Processing Unit (TPU), rackmount solutions like GX4 Rackmount Series, GX8 Rackmount Series, NVIDIA DGX-1, Microsoft' Stratix V FPGA, Graphcore's Intelligent Processor Unit (IPU), Qualcomm's Zeroth platform with Snapdragon processors, NVIDIA's Volta, NVIDIA's DRIVE PX, NVIDIA's JETSON TX1/TX2 MODULE, Intel's Nirvana, Movidius VPU, Fujitsu DPI, ARM's DynamicIQ, IBM TrueNorth, and others.

We claim as follows:
1. A system, comprising:
a federated server comprising a federated server processor and a federated server memory storing federated server instructions that, when executed by the federated server processor, cause the federated server processor to perform an operation of:
receiving group assignability data specifying a plurality of groups assignable to participants in a clinical trial, and group distribution data specifying distribution of the participants into groups in the plurality of groups, the groups including at least one placebo group and one or more treatment groups;
an intervention server comprising an intervention server processor and an intervention server memory storing intervention server instructions that, when executed by the intervention server processor, cause the intervention server processor to perform operations of:

generating group encryption keys for encrypting the group assignability data, the group encryption keys including a public key and a private key;

the federated server instructions further cause the federated server processor to perform operations of:

generating respective group distribution thresholds for each of the groups based on the group distribution data, encrypting the group assignability data using the public key and respective random initialization vectors for each of the participants to generate respective encrypted group assignability data for each of the participants, splitting the group distribution thresholds into a federated server share of the group distribution thresholds and an edge device share of the group distribution thresholds, splitting the encrypted group assignability data into a federated server share of the encrypted group assignability data and an edge device share of the encrypted group assignability data, and generating respective federated server assignments of each of the participants to one of the groups using the federated server share of the group distribution thresholds and the federated server share of the encrypted group assignability data; and respective edge devices of each of the participants, the respective edge devices in communication with the federated server, and comprising respective edge device processors and respective edge device memories storing respective edge device instructions that, when executed by each of the respective edge device processors, cause the respective edge device processors to perform operations of:

generating respective edge device assignments of each of the participants to one of the groups using the edge device share of the group distribution thresholds and the edge device share of the encrypted group assignability data, and respectively combining the federated server assignments and the edge device assignments to produce respective encrypted group assignments of each of the participants to one of the groups.

2. The system of claim 1, further comprising an initializer server in communication with the federated server and the respective edge devices, the initializer server comprising an initializer server processor and an initializer server memory storing initializer server instructions that, when executed by the initializer server processor, cause the initializer server processor to perform an operation of: generating Beaver multiplication triples and respective random floating-point numbers for each of the participants.

3. The system of claim 2, wherein the random floating-point numbers are between zero and one.

4. The system of claim 3, wherein the initializer server instructions further cause the initializer server processor to perform an operation of converting the random floating-point numbers into random fixed-precision numbers.

5. The system of claim 2, wherein the initializer server instructions further cause the initializer server processor to perform an operation of using a bit decomposition protocol to split the Beaver multiplication triples into a federated server share of the Beaver multiplication triples and an edge device share of the Beaver multiplication triples.

6. The system of claim 4, wherein the initializer server instructions further cause the initializer server processor to perform an operation of using a bit decomposition protocol to split the random fixed-precision numbers into a federated server share of the random fixed-precision numbers and an edge device share of the random fixed-precision numbers.

7. The system of claim 5, wherein the initializer server instructions further cause the initializer server processor to perform operations of: delivering the federated server share of the Beaver multiplication triples to the federated server, and delivering the edge device share of the Beaver multiplication triples to the respective edge devices.

8. The system of claim 6, wherein the initializer server instructions further cause the initializer server processor to perform operations of: delivering the federated server share of the random fixed-precision numbers to the federated server, and delivering the edge device share of the random fixed-precision numbers to the respective edge devices.

9. The system of claim 8, wherein the federated server instructions further cause the federated server processor to perform an operation of generating the federated server assignments using the federated server share of the Beaver multiplication triples and the federated server share of the random fixed-precision numbers.

10. The system of claim 8, wherein the respective edge device instructions further cause the respective edge device processors to perform an operation of generating the edge device assignments using the edge device share of the Beaver multiplication triples and the edge device share of the random fixed-precision numbers.

11. The system of claim 1, wherein each of the group distribution thresholds includes an upper distribution bound and a lower distribution bound.

12. The system of claim 11, wherein the federated server instructions further cause the federated server processor to perform an operation of converting, for each of the groups, the upper distribution bound into an upper bound fixed-precision number, and the lower distribution bound into a lower bound fixed-precision number.

13. The system of claim 12, wherein the federated server instructions further cause the federated server processor to perform an operation of using a bit decomposition protocol to split, for each of the groups, the upper bound fixed-precision number into a first part of the upper bound fixed-precision number and a second part of the upper bound fixed-precision number.

14. The system of claim 13, wherein the federated server instructions further cause the federated server processor to perform an operation of using a bit decomposition protocol to split, for each of the groups, the lower bound fixed-precision number into a first part of the lower bound fixed-precision number and a second part of the lower bound fixed-precision number.

15. The system of claim 14, wherein the federated server instructions further cause the federated server processor to perform an operation of generating, for each of the groups, the federated server share of the group distribution thresholds using the first part of the upper bound fixed-precision number and the first part of the lower bound fixed-precision number and the edge device share of the group distribution thresholds using the second part of the upper bound fixed-precision number and the second part of the lower bound fixed-precision number.

16. The system of claim 1, wherein the intervention server is in communication with the respective edge devices, and the intervention server instructions further cause the intervention server processor to perform operations of: receiving the encrypted group assignments from the respective edge devices, and decrypting the encrypted group assignments using the private key to determine respective group assignments of each of the participants.

17. The system of claim 16, wherein the intervention server instructions further cause the intervention server processor to perform operations of: determining, based on the group assignments, whether the distribution of the participants into the groups, as specified by the group distribution data, is met or not.

18. The system of claim 17, wherein, when the distribution is not met, the intervention server instructions further cause the intervention server processor to perform operations of: causing the federated server and the respective edge devices to respectively regenerate the federated server assignments and the edge device assignments to reproduce the encrypted group assignments.

19. A method, including:
receiving, by a federated server, group assignability data specifying a plurality of groups assignable to participants in a clinical trial, and group distribution data specifying distribution of the participants into groups in the plurality of groups, the groups including at least one placebo group and one or more treatment groups;
generating, by an intervention server, group encryption keys for encrypting the group assignability data, the group encryption keys including a public key and a private key;
generating, by the federated server, respective group distribution thresholds for each of the groups based on the group distribution data, to encrypting, by the federated server, the group assignability data using the public key and respective random initialization vectors for each of the participants to generate respective encrypted group assignability data for each of the participants,
splitting, by the federated server, the group distribution thresholds into a federated server share of the group distribution thresholds and an edge device share of the group distribution thresholds,
splitting, by the federated server, the encrypted group assignability data into a federated server share of the encrypted group assignability data and an edge device share of the encrypted group assignability data, and
generating, by the federated server, respective federated server assignments of each of the participants to one of the groups using the federated server share of the group distribution thresholds and the federated server share of the encrypted group assignability data; and
generating, by respective edge devices of each of the participants, respective edge device assignments of each of the participants to one of the groups using the edge device share of the group distribution thresholds and the edge device share of the encrypted group assignability data, and
respectively combining, by respective edge devices of each of the participants, the federated server assignments and the edge device assignments to produce respective encrypted group assignments of each of the participants to one of the groups.

20. A system comprising:
a first non-transitory computer readable storage medium storing first computer program instructions, the first instructions, when executed on a first processor, implement a method comprising:
receiving group assignability data specifying a plurality of groups assignable to participants in a clinical trial, and group distribution data specifying distribution of the participants into groups in the plurality of groups, the groups including at least one placebo group and one or more treatment groups;
a second non-transitory computer readable storage medium storing second computer program instructions, the second instructions, when executed on a second processor, implement a method comprising:
generating group encryption keys for encrypting the group assignability data, the group encryption keys including a public key and a private key;
wherein the first instructions, when executed on the first processor, further implement a method comprising:
generating respective group distribution thresholds for each of the groups based on the group distribution data,
encrypting the group assignability data using the public key and respective random initialization vectors for each of the participants to generate respective encrypted group assignability data for each of the participants,
splitting the group distribution thresholds into a federated server share of the group distribution thresholds and an edge device share of the group distribution thresholds,
splitting the encrypted group assignability data into a federated server share of the encrypted group assignability data and an edge device share of the encrypted group assignability data, and
generating respective federated server assignments of each of the participants to one of the groups using the federated server share of the group distribution thresholds and the federated server share of the encrypted group assignability data; and
respective third non-transitory computer readable storage media each storing third computer program instructions, the third instructions, when executed on each of a set of respective third processors, implement a method comprising:
generating respective edge device assignments of each of the participants to one of the groups using the edge device share of the group distribution thresholds and the edge device share of the encrypted group assignability data, and
respectively combining the federated server assignments and the edge device assignments to produce respective encrypted group assignments of each of the participants to one of the groups.

* * * * *